United States Patent [19]

Sachs

[11] 4,059,010
[45] * Nov. 22, 1977

[54] ULTRASONIC INSPECTION AND DIAGNOSIS SYSTEM

[76] Inventor: Thomas D. Sachs, 34 S. Williams St., Burlington, Vt. 05401

[*] Notice: The portion of the term of this patent subsequent to Nov. 13, 1990, has been disclaimed.

[21] Appl. No.: 589,031

[22] Filed: June 23, 1975

Related U.S. Application Data

[63] Continuation-in-part of Ser. No. 402,163, Oct. 1, 1973, which is a continuation-in-part of Ser. No. 185,306, Sept. 30, 1971, Pat. No. 3,771,355.

[51] Int. Cl.² ......................................... G01N 29/04
[52] U.S. Cl. ..................................................... 73/596
[58] Field of Search .................. 73/67.5 R, 67.6, 67.7, 73/67.8 R, 67.8 S, 67.9

[56] References Cited

U.S. PATENT DOCUMENTS

| | | | |
|---|---|---|---|
| 2,280,226 | 4/1942 | Firestone | 73/67.8 |
| 2,962,710 | 11/1960 | Bellamy | 73/67.7 X |
| 3,233,450 | 2/1966 | Fry | 73/67.8 S |
| 3,250,120 | 5/1966 | Dickinson | 73/67.6 |
| 3,529,465 | 9/1970 | Kleesattel et al. | 73/67.7 X |

Primary Examiner—James J. Gill
Attorney, Agent, or Firm—Eliot S. Gerber

[57] ABSTRACT

A system for the inspection of the internal nature of a material utilizes an exciting ultrasonic field which is directed at a focal point to be inspected and heats that focal point. An ultrasonic sensing beam is directed through the material and through the heated focal point and is received by a transducer. A differential measurement of a propagation parameter of the sensing beam is accomplished by comparing a burst of its ultrasonic waves through the focal point without the heating effect of the exciting field, with an identical burst of the same duration, amplitude and frequency, but immediately after the heating effect has been accomplished by the exciting field. This system may be used to determine tissue characteristics, internal blood flow, and for other medical diagnostic functions.

8 Claims, 6 Drawing Figures

ULTRASONIC INSPECTION AND DIAGNOSIS SYSTEM

This application is an application based on that part of application Ser. No. 402,163, filed Oct. 1, 1973, entitled "Ultrasonic Inspection and Diagnosis System", which is in common with and based upon application Ser. No. 185,306 filed Sept. 30, 1971 and entitled "Ultrasonic Inspection and Diagnosis System", now U.S. Pat. No. 3,771,355. This application, as filed, is a copy of that U.S. Pat. No. 3,771,355 and specific reference is hereby made, under 35 U.S. Code section 120, to both of those above-referenced earlier filed applications.

BACKGROUND OF THE INVENTION

The present invention relates to ultrasonic inspection systems and more particularly to such a system which may be used to map the soft tissues of a patient's body and for other medical diagnostic purposes and for determination of the internal structure of trees.

Present methods of gaining information on the internal structure of trees are largely based on experience, experimental borings, or hammer soundings. The bid made by the lumberman to the owner of a stand of timber depends largely on his estimate of the relative amounts of heartwood and softwood in certain species in that stand of trees. The amount the lumberman is paid for his cut timber depends on the amounts of heartwood and softwood in some species such as maple or white birch which he delivers at the mill. A method of measuring the relative amounts of heartwood and softwood in the standing tree, as well as defects inside the standing tree, could thus be of great utility to the lumberman.

Lumber mills receive logs with essentially unknown internal characteristics and then attempt to cut the maximum usable lumber from each log. An instrument capable of detecting internal tree structure which could act as a data base for computer controlled cutting could maximize the usable lumber obtained from a given log. Some experimentation with presently available echo sounding equipment has been attempted for this purpose, but without much success, for the same reasons which limit the analysis of animal tissues, discussed below.

At the present time ultrasonic inspection systems generally comprise an ultrasonic transducer, such as piezoelectric element which produces bursts of sound waves at a high frequency. The sound waves may be directed as a beam towards the material to be inspected. The material is submerged in a liquid medium along with the propagating transducer and receiving transducer, or both transducers are coupled to the material. The receiving transducer is generally arranged to receive an echo (reflected wave) from the propagated ultrasonic waves. The echoes are analyzed, by amplitude and delay time after the transmitted burst, to determine the nature and depth of the spot being inspected. Such inspection systems, particularly as applied to medical diagnosis, have distinct drawbacks. The information obtained about the nature of the point from which the echo is returned is difficult to analyze because the orientation of the reflecting surface is unknown. In addition, as reflections are returned only from surfaces, large portions of space are totally unrepresented, i.e., those systems do not provide a value for each point of tissue, particularly soft tissue, in space.

There is need in medicine for measurements of soft tissue characteristics in terms of some parameter which is strongly biologically related, and also a great need for techniques which can measure the blood supply in various tissues.

Present methods of gaining information on soft tissues by means of ionizing radiation are largely related to the types of atomic neuclei present in the tissue, rather than any other characteristic of the tissue such as the degree of cell architecture, or the protein content of the tissue. In the case of X-rays the absorption coefficient is heavily dependent on the atomic number of the neuclei present, and thus the bony structure shows up clearly because of its calcium content. But soft tissues are all much alike from the point of view of the absorption of the X-rays. To gain information on soft tissue characteristics, it is necessary to introduce foreign neuclei (elements) of high atomic number into the patient and follow the distribution patterns of these new chemical elements as a way of tracing flows of materials in the body.

In radioactive tracer techniques foreign materials are introduced into the patient, and their radiation followed. Again the information is limited to finding the preferential positions to which these foreign neuclei flow. The properties of the tissue itself and the extent of any neoplasm (cancer) is a matter of conjecture based upon the distortion of the "normal" flow pattern. In addition, the resolution of that method is quite poor, being one centimeter at best.

Various sonic and ultrasonic techniques have been proposed for medical diagnoses, and a number tried. In the low frequency range, auscultation has been a part of the medical arsenal for many years. In the ultrasonic range, transmission methods have been tried with limited success. One difficulty is that the measurement determines the total absorption of the sound beam in going through the entire body, not the absorption at a point. Under these conditions, the bones produce such a large portion of the absorption that the effects of the soft tissue are essentially negligible and, when they are visible at all, they are spatially localized only to the extent that they are somewhere along the rather broad propagation path of the sound beam.

Echo techniques using ultrasonics (referred to as echography in the medical literature) are not the common technique to which reference is made at present when "diagnostic ultrasound" is discussed. These techniques all depend on an incident ultrasonic burst being reflected from a point in the tissue. Echoes or reflected signals occur because of changes in the acoustic impedance of the tissue. Acoustic impedance is the product of the sound velocity and the mass density of the tissue. The more abrupt this change is, the more energy will be reflected as an echo. The magnitude of the echo signals is thus large only for surfaces between tissues and is quite small for soft tissue, as both velocity and mass density are nearly constant in soft tissue. The ultrasonic echogram is thus capable of detecting interfaces, but is not presently capable of measuring the characteristics of every point in the tissue.

SUMMARY OF THE INVENTION

An ultrasonic field, for example, in the form of a cone, is directed through a body immersed in a liquid. The ultrasonic field has a focal point (sensing point) which is heated, for example, a few tenths of one degree centigrade. A second ultrasonic field, in the form of a beam, is the sensing beam and is directed through the body and through the sensing point. A burst of ultrasonic waves of the sensing beam, without the heating effect of the exciting beam, is compared to a burst of such waves immediately after the heating effect of the exciting beam occurs, both bursts passing through the sense point when the exciting beam is off. The sequential bursts travel along the same path but are separated in time, for example, each burst may have a duration of 10 microseconds (be 1.5 cm long) and be separated by 100 microseconds during which time the sending ultrasonic transducer would not produce waves. A comparison, which is a differential measurement of a propagation parameter of the sensing beam, is made between the bursts. The comparison is accomplished by a phase comparator which is connected to (a) the receiving transducer, which receives the sensing beam, and (b) a phase shifter which is connected to the reference oscillator. The reference oscillator is highly stable, on a short-term basis, for example, for a period of one millisecond, preferably in the order of one part in ten billion, i.e., one part in $10^{10}$, and at least one part in $10^8$.

A particular embodiment of this technique, called herein "thermoacoustic sensing technique" (TAST), is the sensing of two different characteristics of living tissues and their distribution in space. The first of these characteristics is the perturbation "P" which is a function of space and time coordinates, with $P = V_T\alpha/\rho C$. $V_T$ is the relative temperature coefficient of velocity in the tissue for the sensing beam. $\alpha$ is the acoustic amplitude absorption coefficient in the tissue for the exciting beam, $\rho$ is the mass density of the tissue, and C is the specific heat capacity of the tissue. $V_T\alpha$, $\rho$ and C are all tissue characteristics which are space and temperature dependent. The second characteristic, referred to as the decay D, is measured by determining the time required for the spatial distribution of temperature produced by the exciting beam at the focal point (sensing point) to decay. This characteristic of the tissue is dependent upon the rate of blood or sap flow in the tissue available to remove this heat, and is thus a measurement of the degree of blood or sap flow in the tissue.

The exciting field is focused and heats the tissue at the focal point more than it does the immediate surroundings. Since this heated volume is in the path of the sensing beam, and the velocity of propagation of the sensing beam depends upon the temperature of the tissue, the wavefront of the sensing beam is distorted spatially, and the signal produced by the receiver of the sense beam experiences a slight phase shift when the tissue has been heated by the exciting field.

The thermoacoustic sensing technique of the present invention can take a measurement at any point in the tissue. Such measurement provides a digital value for each point in space. By moving the two beams in concert, a scanning procedure may be carried out, and a three-dimensional map developed of the tissues in question. The orientation of tissue interfaces does not interfere with the information gathered with this technique.

In Echography, on the other hand, (i) a tissue interface which happens to be oriented in a direction to reflect the energy away from the receiving transducer may not produce any received signal and thus the interface may be missed entirely, and (ii) the acoustic impedance (the tissue characteristic causing the reflections) depends on the mass density and velocity of sound, both of which parameters vary over a relatively narrow range of some 5% in value for soft tissues for the difference in acoustic impedance on the two sides of an interface. Thus, the reflected pressure wave is less than 3% and the reflected energy less than 1/10 of 1%.

The perturbation factor P sensed in the thermoacoustic technique of the present invention depends on the temperature coefficient of velocity, a very strong function of temperature and probably of tissue. The absorption coefficient varies over a large range in soft tissues of the body. In detecting such objects as the edges of infiltrating tumors, the tissue characteristics vary slowly with space and are therefore almost completely invisible to Echography, while the variations can be traced out numerically by the thermoacoustic technique because it makes a measurement at every spacial point.

I. GENERAL DESCRIPTION OF THE SYSTEM

Figure 1:
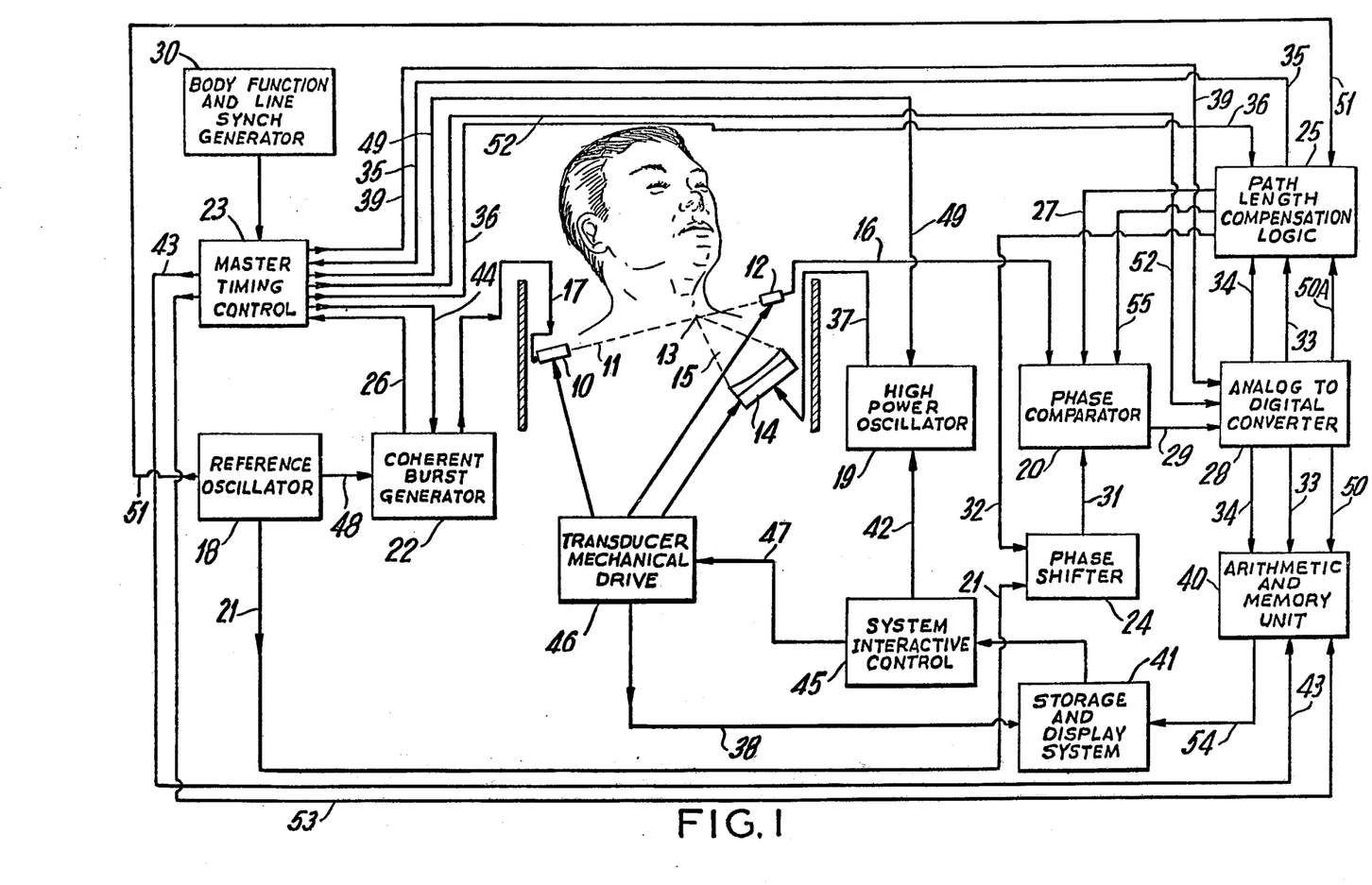
FIG. 1 is a perspective view of the system of the present invention combined with a block diagram as used in medical diagnosis.

As shown in FIG. 1, the portion of the person's body to be diagnosed — in this case a neck (Thyroid) — is submerged in a tank of ultrasonic wave conducting liquid, preferably water, such as Ringer's solution or tap water. A first transducer 10, suitably a well damped piezoelectric ceramic or crystal, produces a collimated or directed beam 11 in the ultrasonic range, suitably 100 kHz to 15 mHz, depending upon the application. Preferably the piezoelectric material is one with a high electromechanical coupling coefficient, and whose acoustic impedance is matched to a backing with high loss characteristics in order to produce a well damped system. A suitable transducer could also be a disk of the ceramic PZT-4 of Clevite Corp., Cleveland, Ohio, backed by a brass bar which is physically long compared to the physical length of the acoustic burst, and so terminated as to prevent reflections.

The beam 11 is directed through the neck and is picked up by the receiving transducer 12, which also is suitably a piezoelectric ceramic transducer of like structure but smaller in diameter than transducer 10. This first beam, called the sensing beam, passes through the sense point 13 whose characteristics are to be analyzed. A third transducer 14, also suitably a piezoelectric crystal or ceramic, produces a second focused ultrasonic field 15, called the exciting field. The transducer 14 is either a shaped ceramic, chosen so as to focus the beam, or a ceramic or crystal plate combined with an acoustic lens. Preferably the field 15 is in the form of a cone having a focal point. Preferably the field 15 is at a different frequency than the beam 11, preferably 100 kHz to 15 mHz, depending on the application.

The two beams are so aimed that they would cross at the sense point if both of them were operational at the same time (which they are not). The receiving transducer 12 contains an integral amplifier, to prevent signal fluctuations from physical motion of the cables, which amplifier then feeds a coaxial cable 16 leading to the phase comparator 20. The sending (transmitting) transducer 10 is connected, via line 17, to a coherent burst generator 22 which generates an appropriate burst. The inputs to the burst generator 22 are a trigger signal on line 44 from the master timing control 23, and a very stable continuous RF signal, over line 48, from a very stable high frequency reference oscillator 18. The coherent burst generator 22 generates a phase coherent gate, i.e., a start and stop signal in which the beginning and end of the burst are synchronous with the continuous R.F. supplied on line 48, providing the period the burst should be on. That gate signal, on line 26, is received by the master timing control 23.

The master timing control 23 sends the burst timing signals (start and stop of the burst appropriately delayed) (a) to the phase comparator 20 via the propagation path length compensation logic 25 and line 27; (b) over line 39 to the analog to digital converter 28; and (c) over line 36 to the path length compensation logic 25. The path length compensation logic 25 keeps track of the elapsed time by counting the oscillations from the precision oscillator 18, supplied via line 51, for example, using a second coherent time delay generator of the type shown in FIG. 5.

Figure 6:
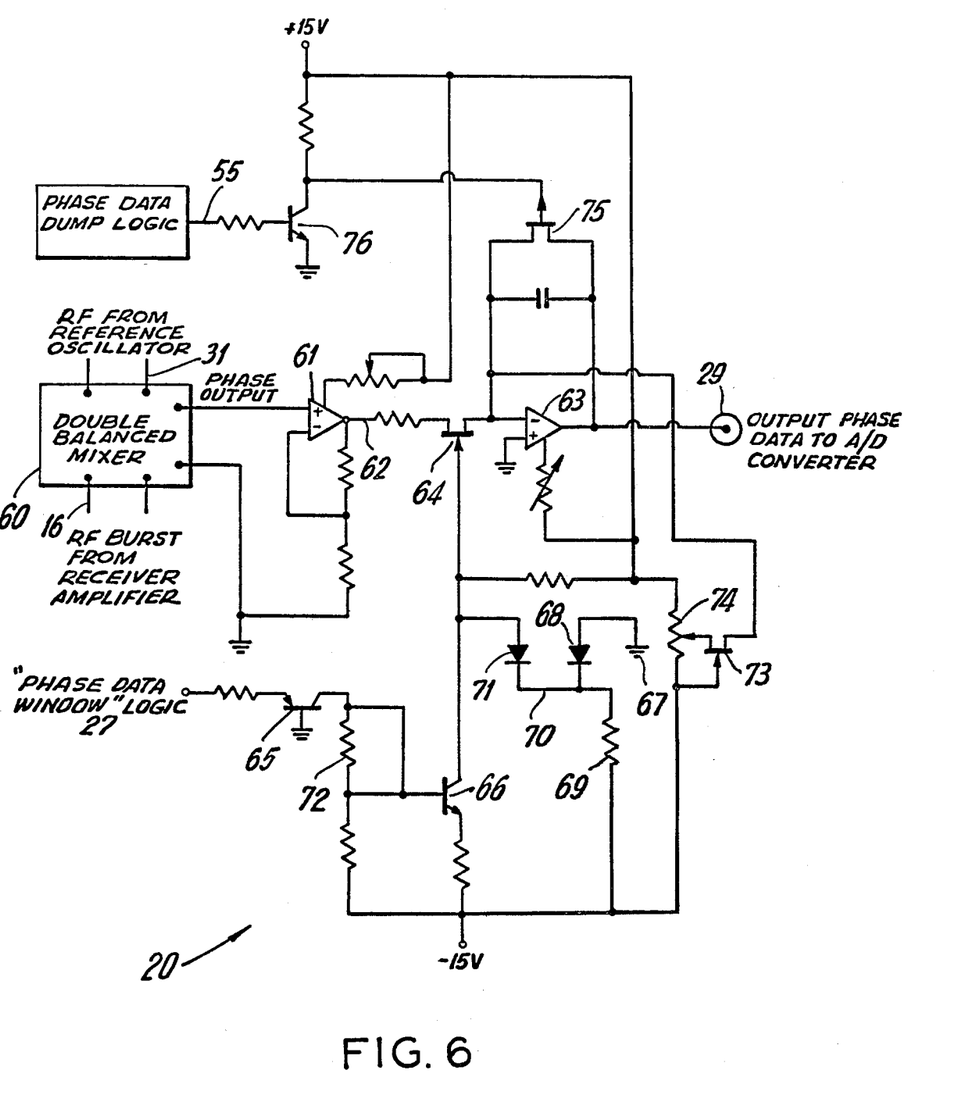
FIG. 6 is a circuit diagram of the phase comparator.

Shortly before the sense burst 11 arrives at the receiving transducer 12, the zeroing and old data destroying signal present on line 55 must be removed, as shown in FIG. 6, so that the phase comparator is both zeroed and able to accept new data. Approximately one oscillation before the sense burst 11 arrives at the receiving transducer 12 the path length compensation logic supplies the data window signal on line 27, see FIG. 6. This signal arms the phase comparator 20 to accept new data, over line 16. This gate signal, from the path length compensation logic 25, keeps the phase comparator 20 active until approximately one oscillation after the sensing burst signal disappears from line 16.

The phase output signal from the phase comparator 20 appears on the output line 29 and goes to the analog to digital converter 28, which overscales very easily and frequently at maximum sensitivity and, when this happens, then produces a signal on line 34 to the path length compensation logic 25. At the same time the sign of the overscale is fed, by line 35, to the master timing control 23, 20 that the sensitivity of the analog to digital converter should be decreased to a minimum which is then accomplished by the master timing control 23 over line 52.

The next sense beam burst will provide a digital output from the path length compensation logic 25, to phase shifter 24 on line 32, giving both the direction and magnitude by which the phase reference (from the stable oscillator 18 through line 21 to the phase shifter 24) should be shifted by the phase shifter 24 before being fed through line 31 to the phase comparator 20. Now that the system has been zeroed, the master timing control 23 increases the sensitivity of the analog to digital converter 28 by line 52, making corrections as needed to the phase shifter 24 as the sensitivity is increased, until maximum sensitivity of the sense beam system is reached. If the phase shifter 24 is now kept at a constant value, through holding the digital value on line 32 fixed, and a perturbation is applied to the system by the exciting field, the shifts in the output of the analog to digital converter are a direct measurement of that perturbation.

II. DESCRIPTION OF DETAILS OF THE CIRCUITRY

Many circuit blocks of the system shown in FIG. 1 are conventional and known to skilled men in the art so that detailed circuit diagrams would only unduly lengthen the specification. However, some of the circuit blocks of that system are less conventional and are described below.

Introduction

It is not possible to make a highly stable burst oscillator because of the starting transients which inevitably occur whenever an oscillator is turned on. Instead, it is necessary to run the reference oscillator 18 continuously and gate out appropriate portions of its signal under control of the coherent time delay generator included in the coherent burst generator 22 and shown in FIG. 5. The coherent burst generator, seen as a whole, provides a burst of bipolar square cornered waves such as those shown in FIG. 5, waveform on line 17, which are synchronized with the oscillator and occur at approximately the time desired (within one RF period). The actual time the burst starts then becomes the time reference for the rest of the system. Because of its square cornered nature, this output signal is very rich in odd harmonics of the desired signal. It has been found that one can, nevertheless, make a phase comparison of the signal in the received acoustic burst, using the sinusoidal reference signal from oscillator 18, and obtain an adequately stable output signal from the phase comparator 20 despite the preference of these unwanted harmonic components in the signal supplied to the transmitting transducer 10. The reason this is possible is that the transmitting and receiving transducers 10 and 12 act as filters, as does the medium itself, in absorbing the higher frequencies much more strongly than the lower frequency, which lower frequency is the signal of interest.

Figure 5:
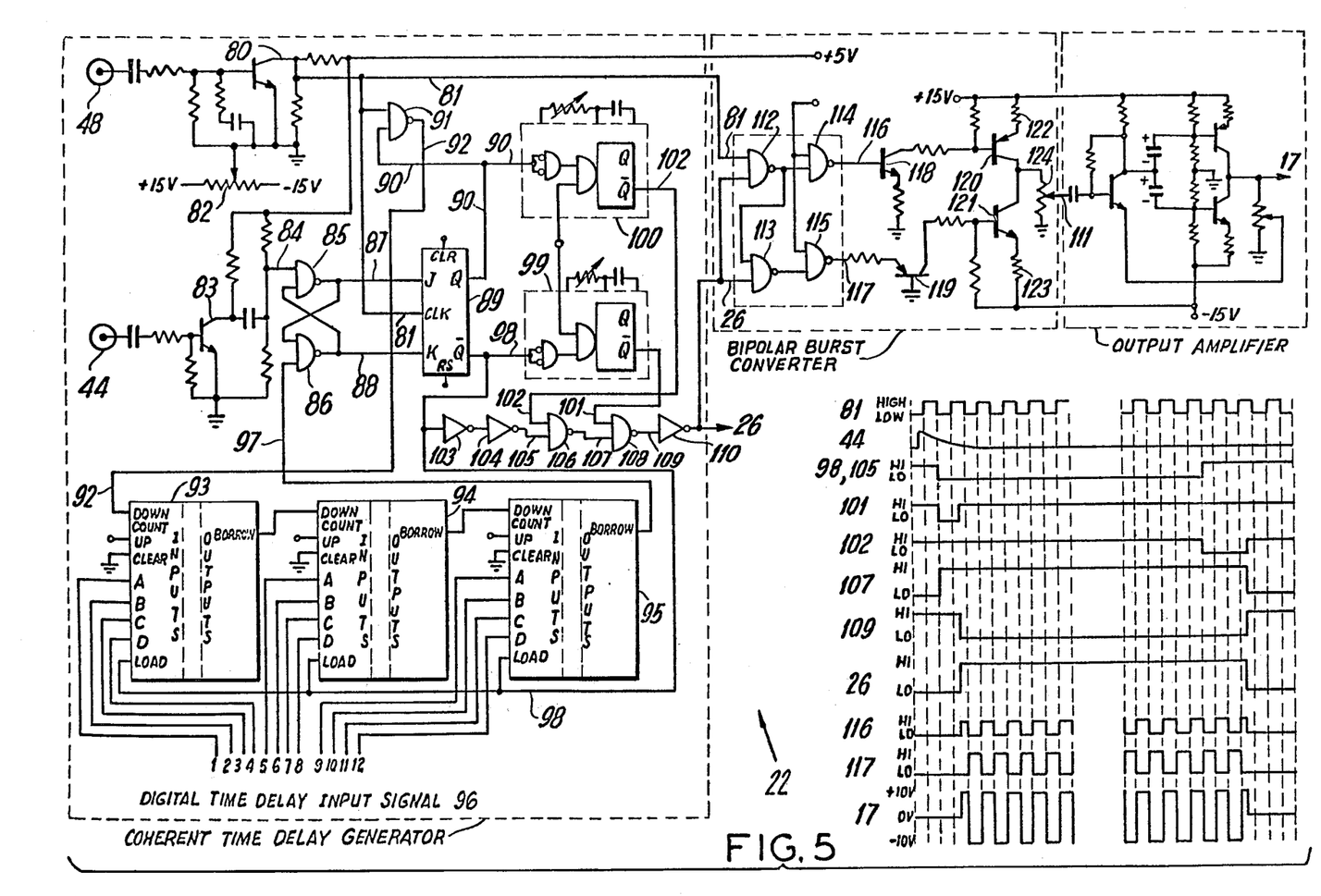
FIG. 5 is a circuit diagram of the coherent burst generator.

The reference signal from the oscillator 18 must exist at the same time that the burst sent from transducer 10 arrives at transducer 12, which is about 700 microseconds for a spacing of one meter between these transducers. The reference signal must also stay completely stable within this time period so that a phase comparison is possible. Since the reference oscillator signal is used in the sensing beam and also in the path length compensation logic, a phase shift of 360° seen at the receiver can be compensated by shifting the delay generator, which depends upon this signal and is phase synchronous with it, by one full oscillation. This is accomplished by changing a digital number supplied to the phase coherent delay generator by one unit. This number is shown in FIG. 5, Number 96.

A. The Reference Oscillator 18 And the Frequency Of Operation

The reference oscillator 18 is an extremely stable high frequency turnable oscillator. A suitable type has a stability of one part in $2 \times 10^{10}$, a frequency range of 0.1-15 M Hz, and may be obtained, under Model No. 5100B/5110B, from Hewlett Packard of Palo Alto, Calif.

The frequency of operation of the reference oscillator 18 will vary with different applications since it is always that of the sense beam. The frequencies of the sensing beam and exciting field may be the same or different. Two to five Megahertz are frequencies frequently used in the brain. For studies in the abdomen, frequencies as high as five Megahertz are usually not very useful because of the depth through which the beams must be propagated and the increase in absorption coefficient which occurs with higher frequencies. In the eye, frequencies of the order of 15 mhz are useful because the aqueous and vitreous humors have low absorption coefficients and by using very high frequencies smaller objects can be picked up. For example, high resolution may be obtained by firing the exciting field in through the front of the eye with a frequency of 15 Mhz while being forced to go down to 1 Mhz or lower for the sensing beam to enable it to pass through the bone without excessive losses.

B. The Phase Comparator 20

The basic element of the phase comparator 20, see FIG. 6, is a double-balanced mixer 60 which delivers an output of 0 volts when the radio frequency signals from the reference oscillator 18, via the phase shifter 24 and line 31, and the receiver amplifier 12 are in phase. An operational amplifier follower with gain 61, for example, of the type MC1433G (Motorola) delivers an amplified signal at its output 62, which amplified signal is free of most of the RF leakage signal coming from the double balanced mixer 60 because of the limited frequency response of the operational amplifier. This amplified signal is then fed to the gated integrator 63, for example, a QFT-5 operational amplifier (Philbrick-Nexus) in the configuration shown. During the time when the N channel field effect transistor (Type 2N5459) 64 has low resistance, the signal from the output of the operational amplifier 63 is integrated, delivering an output on line 29 having a polarity opposite to that of the voltage fed out of the double balanced mixer 60. The gate of FET 64 operates at ground when the input signal on line 27 is at 0 volts, and thus the two transistors 65 and 66 are both turned off. Under these conditions, positive current flows from the ground terminal 67 through the diode 68 (Type IN914) to the −15 volt line through the 1.5K resistor 69. This determines the voltage on the line 70 connecting the two diodes 68, 71 as being one diode offset voltage negative with respect to ground. The gate of the FET 64 will be one diode drop positive with respect to line 70 because of the current flowing from the −15 volt supply through the 2.7K resistor 72 and diode 71. Thus the gate of the FET 64 will be at ground potential whenever the input on line 27 is at logical 0. When line 27 exhibits a logical "1", both of the connecting transistors 65, 66 are turned on, the transistor 66 delivers a current of about 10 milliamperes and draws the gate of the FET 64 (Type 2N5459) to approximately −10 volts, thus switching the FET 64 to a high resistance state. In this condition the integrator system is switched into a "hold" mode, holding the integral developed from the most recent burst (at the output 29) while the analog to digital converter is operating.

In this hold condition, the drift of the output of the operational amplifier gated integrator 63 can be set to zero by the current source which feeds its negative input terminal. This extremely low current source is supplied by using the cut-off FET (Type 2N5457) 73 as a very high resistance ($10^{10}$ ohms) in series with a voltage supplied by the hold drift adjust potentiometer 74. This source supplies sufficient current to compensate for bias currents and leakage currents at the negative input terminal of the amplifier 63 without being unduly sensitive to humidity, fingerprints or adjustment. Once the analog to digital converter 28 has converted the output on line 29, the system must reset itself to zero in preparation for the next measurement. This is done by shorting the integrator condenser with the P channel FET 75 (of Type 2N5462) which is turned on by driving its gate to approximately zero volts, which occurs when a logical "1" appears on line 55, thus turning on the transistor 76. Assuming that the two input signals are cos wt and cos $(wt+\phi)$ the output signal will be Sin $2\phi$. Assuming that we hold the phase shift between the two input signals to a very low value, we may approximate Sin $2\phi$ by $2\phi$, so that the output of the phase comparator is linear with phase for small phase angle differences between the reference oscillator and the received burst.

C. Coherent Burst Generator 22

The coherent burst generator consists of three portions: a coherent time delay generator shown on the left in FIG. 5, a bipolar burst converter, and an output amplifier.

Coherent Time Delay Generator. The coherent time delay generator requires three inputs. In the case of the coherent burst generator 22, the numbers of the connecting lines are shown as in FIG. 1, but this time delay generator is also used in the path length compensation logic 25 where different connecting line numbers will be applicable. The delay generator requires a digital number input telling it how many oscillations it should count before it ends its output pulse. In the case of the coherent burst generator 22 this number is set once and left during the entire analysis process, but in the case of the path length compensation logic 25 and its interaction with the phase shifter 24, phase shifts exceeding 360° are compensated for by changing the digital number being fed to the coherent time delay generator.

Referring now to FIG. 5, the input from the stable oscillator arrives at 48 and is capacitively coupled into the base of the NPN transistor 80 and is developed on line 81 as a square wave because transistor 80 is overdriven. The symmetry of this square wave is controlled by adjusting the bias on the base of transistor 80 with the potentiometer 82. This symmetrized square wave becomes the input to the bipolar burst converter, and also to the counting circuits in the coherent time delay generator, all of which are referred to as line 81. The positive transient delivered to input 44 starts the operation of the coherent time delay generator by first being amplified, inverted, and differentiated in the circuit related to transistor 83 and thus switching the R S flip-flop (consisting of NAND gates 85 and 86) into the state where line 87 is high and line 88 is low. These two lines feeding the J-K flip-flop (Texas Instruments SN 7472N) 89 prepare it to switch its Q output on line 90 high on the next negative transition on the clock input line 81 from the RF signal. Thus the activation of gate 91 occurs on the negative transition on line 81, so line 92 stays high for one half cycle of the RF on line 81, and then switches low on the first positive transition on line 81 after the first negative transition on that line which follows the trigger pulse on 44. The negative transition on 92 is not counted by the four-bit presettable up-/down counter, which is here used as a presettable down counter 93 (Texas Instruments SN 74193N). Counter 93 waits still another half cycle until the positive transition occurs on line 92 and then it triggers. How far the presettable down counter consisting of 93, 94 and 95 counts before passing through zero depends on the digital number at the digital time delay input signal 96 and determines the number of pulses on line 92 counted before the output line 97 transitions from high to low and in so doing resets the RS flip-flop consisting of gates 85 and 86 so that the output Q of 89 on line 90 goes low on the next negative transition on line 81. Thus the output of 89 is phase synchronous with the RF signal on 81 and is determined by a combination of the input start signal at 44 and the digital time delay signal on 96 and the frequency fed in at input 48. The counters are reloaded from 96 between bursts when line 98 goes low.

The time slot specified by 89 on lines 90 and 98 starts and stops at a specified phase with relation to the oscillator signal fed in on line 81, but the phase of the R.F. at which these transitions on lines 90 and 98 occur is not adjustable. To make the starting and ending phases adjustable, two one-shot multivibrators (Texas Instruments SN 74121N) 99 and 100 take inputs respectively from lines 98 and 90 and give outputs respectively on lines 101 and 102. The waveforms occurring on these lines are shown in the sketch of waveforms on FIG. 5. Waveform 98 is delayed by two gate delays (103,104) and becomes the waveform on line 105 after a delay of some 20 nanoseconds. This delay is necessary to prevent a glitch on line 107 which would otherwise occur when line 98 transitioned positively just before line 102 transitioned negatively. Gate 106 has combined the "stop delay" from 100 with the time slot from 89 to form the waveform on line 107. The "start delay" is combined with the signal on line 107 by 108 which forms the signal on line 109. The waveform on line 109 has its beginning delayed by one shot 99, and its end delayed by one shot 100. Thus the controls on one shot 99 and 100 become the phase control adjustment on the beginning and end of the output delay time, respectively. The signal on line 109 is inverted by 110 to become the signal on 26 which is the output of the coherent time delay generator to both the bipolar burst converter and the master timing control 23.

Bipolar Burst Converter. The purpose of this circuit is to convert two monopolar signals (signals having either zero volts or +3 volts such as TTL logic levels) into a bipolar burst, i.e., one which starts at 0, then swings alternately positive and negative during operation, and returns to zero after the burst is over. Such a pair of signals are those appearing on lines 26 and 81. A monopolar burst signal can be broken down into two components, an RF burst of bipolar square waves, and a superimposed square wave of the length of the burst. The superimposed square wave, if applied to the transducer, will be differentiated and will lead to beginning and ending transients in the acoustic burst. Since the transducer 10 is a resonant system, albeit a low Q one, any variation in beginning or ending phase, or inappropriate beginning or ending phase, will generate transients in the burst which will interfere with the operation of the phase comparator 20 and thus generate unnecessary noise.

The inputs from lines 81 and 26 are fed to the bipolar burst convertor (FIG. 5) and the output appears at line 111 with the waveform shown on 17. Between bursts line 26 is low which guarantees lines 116 and 117 low and thus transistors 118, 119, 120 and 121 are turned off and no current flows through the output resistor. There is therefore zero voltage on line 111 between bursts. When line 26 goes high during the burst, gates 112 and 113 become simple inverters with 112 feeding 113; thus, the output on these two gates are complements during the burst. The outputs of gates 114 and 115, which are connected simply as inverters, are thus also complementary during the burst and zero between bursts. If, for example, line 116 is high, then transistor 118 is turned on, acts as a constant current source, and supplies a fixed voltage at the junction of the two resistors feeding the base of transistor 120. 120 is in turn a current source delivering a current to the output resistor 124 and pulling line 111 positive to a voltage fixed by resistor 122. At this same time transistors 119 and 121 are turned off. During the other half of the RF cycle applied at 81, the situation reverses and transistors 118 and 120 are turned off while 119 and 121 are turned on, 119 acting as a current source for 121 which thus supplies a fixed output current which draws line 111 negative to a fixed potential with respect to ground, which potential is set by current source control resistor 123. Thus there is a swing on 111 both positive and negative with respect to ground which is the same as that shown as occurring on line 17. In order to make certain that no transient producing pulse remains, positive and negative excursions of the signal on line 111 must be identical. The magnitude of the positive and the negative swings are adjusted by resistors 122 and 123 respectively.

Output Amplifier. The output amplifier is a feedback amplifier of considerable bandwidth which can swing both positive and negative with respect to ground and is capable of driving a transducer with an impedance as low as 200 ohms. It is capable of approximately ½ watt output.

Construction

It should be noted that the physical construction of all of the parts of the coherent burst generator may be critical. Preferably the circuits should be built on a printed circuit card in which very heavy lands are used for all connections with large areas of metal left in place and grounded between signal leads to act as shielding.

System Timing. Once the coherent burst generator has received its start signal on line 44, it waits until the RF phase of the oscillator is proper and then delivers a transition to a logical "1" on line 26 telling the master timing control 23 that the burst has started. At the end of the appropriate number of oscillations, including correct phasing at the beginning and end of the burst to prevent transducer 10 from producing transients at these times, the signal on line 26 again goes to logical "0" indicating to the master timing control that the burst has ended. This information is in turn fed by the master timing control 23 to the path length compensation logic 25 via line 36, which allows the necessary time for the signal to propagate from transducer 10 to transducer 12. The time delayed gating signal on line 27 is produced by another coherent time delay generator (slightly simplified from that in FIG. 5 since phase synchronization has already been achieved) which is in the path length compensation logic. A gating pulse started by this delay generator is supplied on line 27 to the phase comparator 20 as the "data window" which tells the latter system when to accept data. Thus spurious signals arriving from the receiving transducer 12 at any but the correct time will be ignored by the system.

The time delay required for the signal to pass from transducer 10 to transducer 12 depends principally on the amount of tissue being penetrated and the velocity of the sensing beam in that tissue. The propagation time between the transducers changes as a function of the materials between them (patient movements) and it is necessary to compensate for these varying transit times accurately enough so that the output of the phase comparator is always near 0, which implies a very high degree of precision in this compensation. It is for this reason that the path length compensation logic is required, and that the digital time delay generator within the path length compensation logic is insufficient by itself, and must be coupled with control to the phase shifter 24 in order to achieve adequate precision both in the placing of the "data window" just around the received burst (in time) and also to hold the output of the phase comparator very close to zero as required.

III. Operation of the System

Velocity Measurement Technique

The sense beam burst 11 is generated by gating a portion of the signal from an extremely stable oscillator 18 (running at the desired acoustic frequency) so that the burst's beginning and end are phase coherent with the oscillator. The burst is then applied to the transmitting transducer 10, propagated through the tissue and picked up by the receiving transducer 12. After amplification the signal is fed, via line 16, to a phase comparison system 20 where it is compared with the phase corrected oscillator signal on line 31. The output of the double-balanced mixer 60 is amplified, integrated over the period of time when the burst is appearing at the receiving transducer (circuitry in FIG. 6), and the integral digitized and placed in memory. The perturbing beam 15 is now applied. After the tissue has been heated by the perturbing beam 15, another sense beam burst 11 is generated and handled identically by the same electronic system through the digitization process. When this second result is placed in memory, however, it is subtracted from the first one. The resulting digital difference is proportional to the perturbation of the biological medium by the perturbing beam 15 and thus is proportional to the following: The P factor at the focus of the perturbing beam, the intensity I of the perturbing beam at its focus, the period of time the perturbing beam is turned on $\tau$ and the sense beam's path length through the region affected by the focus of the perturbing field (which is the same as the diameter of the perturbing beam's focus $d_f$). This digital difference is a measure of the time delay of the sensing beam caused by the perturbation, and its value $t_d$ can be shown to be:

$$t_d = \frac{2\tau}{JV} \int_{-\infty}^{+\infty} I_o(x,y,z) P(x,y,z,T,f_p) \, dx \quad 1$$

where $$P = \frac{1}{\rho CV} \frac{\alpha V(x,y,z,T)}{\alpha T} \alpha(x,y,z,T,f) \quad 2$$

and $1/V \, \delta V/\delta T$ is the relative temperature coefficient of velocity, $\alpha$ is the acoustic amplitude absorption coefficient, $\rho$ is the mass density, and C is the specific heat of the tissue $\tau$ is the temporal length of the acoustic perturbing burst, J is 4.186 Joules per calorie, and $V$ is the velocity of sound.

The fluctuations of the electronic and acoustic systems are reflected in the digital number proportional to $t_d$. The deviations of these values from the average value of $t_d$, $t_d$ are $\delta t_d$. The number of possible gradations G of $t_d$ which can be meaningfully distinguished when making a single measurement will thus be $G = t_d/\delta t_d$.

The value of G can be increased by signal processing techniques, such as described below. Making N measurements and averaging them, the noise level will drop by $\sqrt{N}$ so that the number of meaningful gradations becomes:

$$G = \frac{\bar{t_d} \sqrt{N}}{\sigma t_d} \quad 3$$

The line integral in equation 1 is to be carried out along the sense beam's path 11 over spatial variations in the intensity of the perturbing beam 15. Assuming that this intensity is I in the interaction region and zero everywhere else, and combining Equations 1, 2 and 3, we obtain:

$$G = \frac{2\sqrt{N} \, \tau I d_f P}{J V \sigma t_d} \quad 4$$

where $d_f$ is the diameter of the focal zone of the perturbing field and is thus the length of the perturbed medium through which the sensing beam passes.

Tissue Reaction

The exposure of the patient is $E = \tau I$ where $\tau$ is the time of application of the perturbing beam and I is the intensity in Watts per square Centimeter. Thus E is proportional to the total energy passing through the tissue and also to the temperature rise. $\tau$ may be the time of a single burst, if only one is applied, or may be the sum of burst times in which case it is referred to as the summated irradiation time.

If one uses a single burst of perturbing field 0.1 second long and 100 Watts/cm$^2$ in intensity, the exposure parameter of 1% of that required to produce lesions from the published criteria quoted below. The TAST technique requires only a single burst of the perturbing beam to obtain information at a single point in space because the information is recorded digitally and may be made available for display later as needed. Far lesser exposures could be used, if desired, at the cost of degradation of either spatial or tissue type resolution.

Clinical Optimization

The clinical implications of Equation 4 are easier to see when it is rewritten in the form:

$$G = k\sqrt{N} E \, d_f P \quad 5$$

where $k = 2/JV\delta t_d$ is a constant for this analysis, since the average velocity of sound in the tissue is not susceptible to our control and the noise level $\delta t_d$ for a single measurement is considered fixed. E is the exposure parameter $I\tau$ which is proportional to the heating and on which the reaction of the tissue depends in part under conditions specified by the Fry et al and Taylor (Fry et al, J. Acoust. Soc. AM. 48 (Part 2) 1413 (1970) and Taylor J. Pathology (Edinburgh) 102 41 (1970). The diameter of the focal spot produced by the perturbing field is $d_f$, which is a measurement of the spatial resolution of the system, and is inversely proportional to the frequency of the perturbing field. P is the perturbation factor, a tissue parameter which is proportional to the frequency of the perturbing field. N is the number of measurements carried out and averaged by the system. 1000 measurement pairs can be carried out in 0.1 seconds, so N can easily be of the order of 1000.

For a clinically useful system, one must satisfy the following conditions: 1. Be able to distinguish as many gradations of tissue characteristics as possible, i.e., maximize G. 2. Keep the exposure E to safe levels. 3. Have a high spatial resolution, i.e., keep $d_f$ small. 4. Hold N to a reasonable value so that the scanning process does not take too long and motions of the patient are not too important. The feasibility of the technique depends on finding a regime in which all of these conflicting conditions are adequately satisfied.

We shall approach the problem by calculating G, assuming a set of reasonable values for the other parameters. For E, we take a value of I of 100 watts per cm² and $\tau$ of 0.1 seconds. We choose the perturbing beam frequency $f_p$ as 2 Mhz which implies a focal point diameter $d_f$ of 0.2 centimeters which then implies a resolution of the order of one millimeter. N is chosen as 1000, and thus the signal processing time is about equal to the perturbing burst time. The velocity of sound in brain (temperature unspecified) or water at 37° C is V = 1.6 × 10⁵ cm/sec., $\delta t_d$ is taken as the noise level for a single measurement and is about $36 \times 10^{-12}$ seconds from our experience. It is assumed that the relative temperature coefficient of velocity in tissues will be that of water, i.e., at 37° C it is $9.94 \times 10^{-4}$°C$^{-1}$. The absorption coefficient for tissues such as brain, liver or kidney at 2 Mhz is about 2 db per centimeter or 0.231 Nepers/cm. Assuming density and specific heat to be roughly those of water, we find a P factor of $2.3 \times 10^{-4}$ cm²/calorie. For striated muscle the value would be roughly double this, while for fat it would be roughly half. For blood the value should be about one fifth of that for brain. On the other hand, Meningiomas should have $4 \times 10^{-4}$ cm²/calorie, if one corrects for the frequency differences in the absorption data available at this time.

Solving for G in equation 5 using $P = 2.3 \times 10^{-4}$ cm²/calor under the above assumptions, one finds that G = 1200. Since we need only a G value of 2 or 3 to distinguish fat from brain, or brain from striated muscle, and only a G value of 1 to distinguish brain from cyst or meningioma from cyst, this result indicates that an extremely high P value resolution is available if needed. If such a high resolution as to types of tissue (P value) is not needed, one could cut down the exposure factor in exchange for lower P value resolution.

In assuming that $d_f$ is 2 mm, we are implicitly assuming that the limit of resolution of the system is about 1 millimeter. If this degree of spatial resolution is not needed, the focus of the perturbing beam could be broadened, and the required exposure reduced, or if the exposure is kept constant and the focus broadened, the P value resolution G may be increased.

IIIA. Operation of the System - Scanning

In order to scan for the values of different points in the body, the system interactive control 45, which is basically a computer, now orders, via line 47, the exciting field transducer 14 moved by the mechanical drive system 46 so that it is still aimed along the sense beam but is at a different position. In this system one must check to see whether the output of the phase comparator as indicated by the last analog to digital conversion is of such a value that there is space for another shift in the phase without running the analog to digital converter 28 off-scale. If such space is available, then the tissue measurement process referred to may be repeated for this new point in space and the appropriate values for P and D recorded in the storage system 41. Should it happen that the next measurement would overscale the analog to digital converter, then the propagation path length compensation logic 25 reactivates itself.

The phase shifter 24 is readjusted by the propagation path length compensation logic 25, as described above, until the output of the analog to digital converter is again close to zero. Such readjustment is accomplished over a series of sense bursts, starting with the sensitivity of the analog to digital converter 28 set at its lowest point, through line 52, since the propagation path length compensation logic 25 has informed the master time control 23, through line 35, that this condition exists, and the master timing control has then shifted into the zeroing timing sequence. In case the phase shift has exceeded 360°, the propagation path length compensation logic 25 also changes the delay time for the propagation of the sense beam burst by the time required for one full oscillation, this correction being made digitally in the digital time delay system (FIG. 5) which operates on the acoustic sense beam frequency, and this requires only a simple logic level change. Now that the system has been rezeroed, the process may be restarted. After the entire length of the sense beam within the tissue has been scanned, the sense beam may be moved to a new position, and a new scan started.

New settings for the time delay and phase shifter settings will be required because of the new thickness of the tissue through which the sense beam now passes. This correction could in principle be made manually, but preferably is made electronically by comparing the time of arrival of the sense beam burst with the digital time delay system and thus determining the number of oscillations to be counted directly, switching to this time delay, and then following the system to go through its standard phase signal zeroing procedure quoted above.

The body function and line synch generator 30 monitors the pulse and respiration of the person under test and selects a time with reference to these two parameters and the power line phase at which to make measurements. Since motions of the patient constitute noise in the system output, it is important that measurements be made at times when minimum motion is occurring. At the same time there are certain phases of the power line during which large amounts of impulsive noise are present because of switching transients of line synchronous switching devices, such as silicon controlled rectifiers. To avoid this noise in the system, it in convenient to make all measurements at such phases of the AC line where such noises will not interfere.

The body function and line synch generator first generates a time signal when the waveform with the longest period, namely, the respiration, reaches a quiet phase, then observes the pulse, and when it has reached a quiet phase, switches its attention to the AC line, and when it in turn has reached a quiet phase, supplies the basic system trigger which starts the master timing control system. It is probable that where long delays are required, repeated references to the body function and line synch generator will be necessary to assure a maximally quiescent state of both the body and the electrical environment.

IIIB. Operation of the System - Averaging

A method of utilizing this system to carry out signal averaging in order to reduce noise will be described below.

Figure 2:
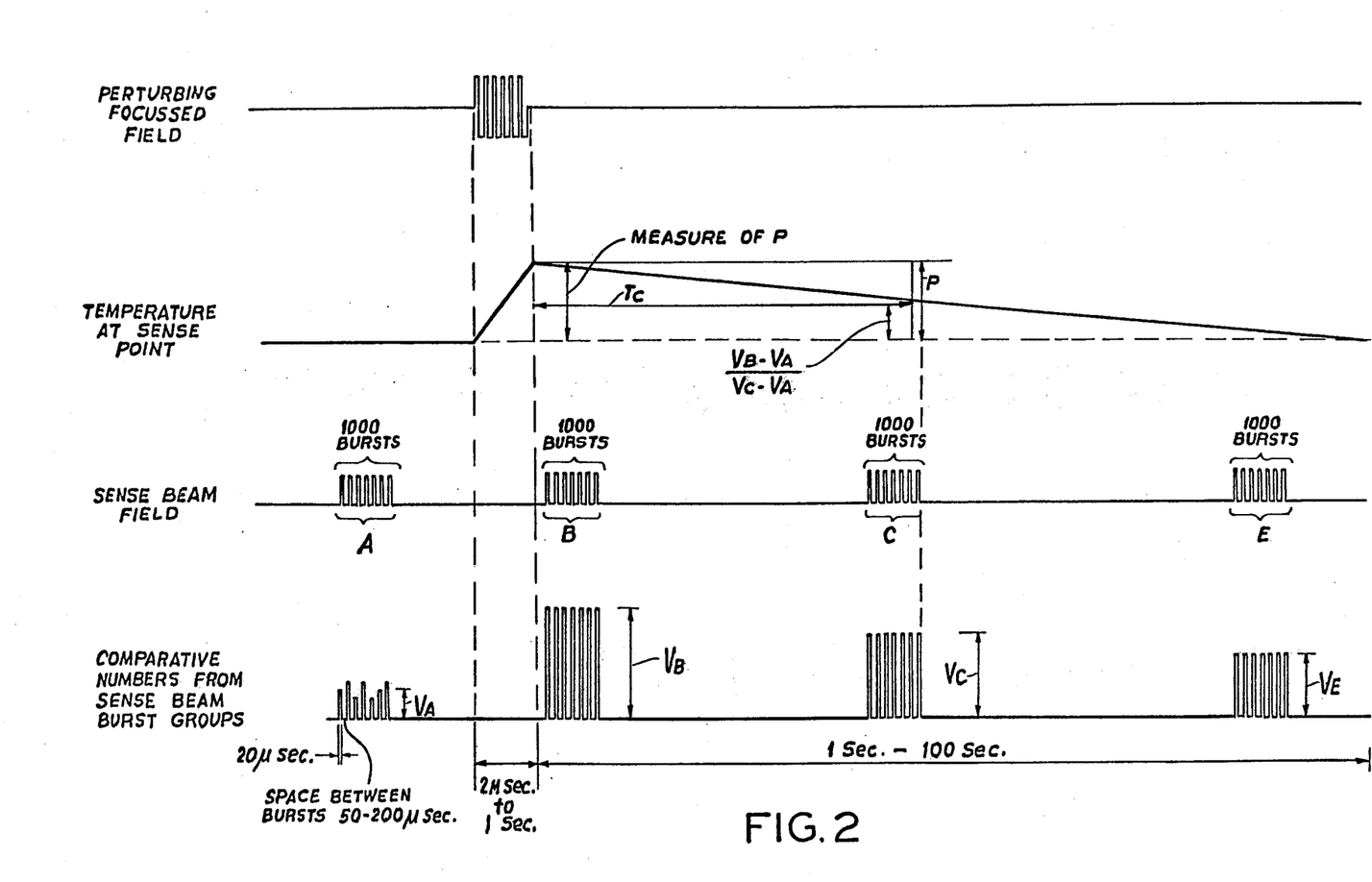
FIG. 2 is a timing diagram showing in principle how the signal processing occurs for measuring the parameters P and D at one point in tissue.
Figure 3:
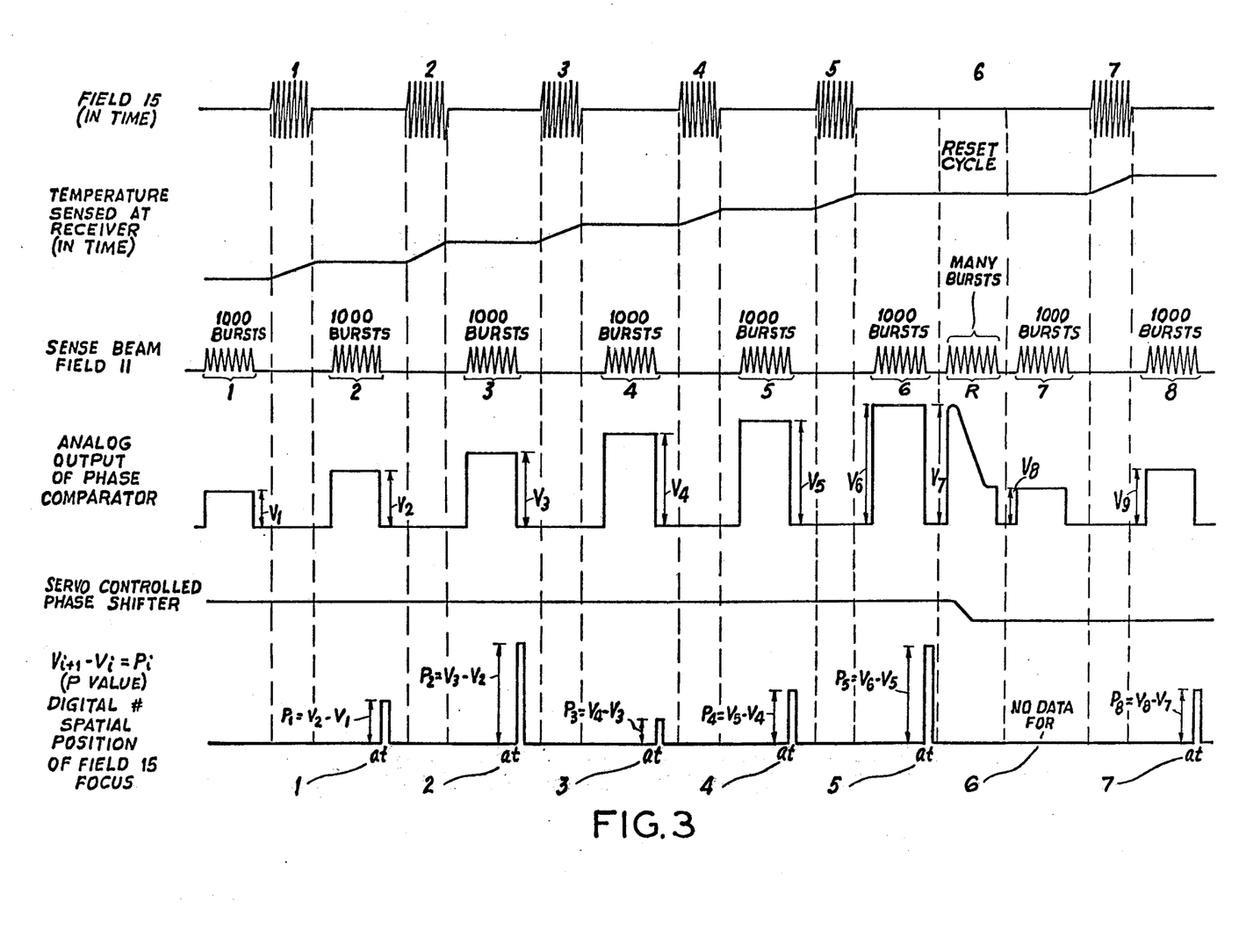
FIG. 3 is a timing diagram showing the multiple perturbation of the tissue at various points to allow line scanning of the sense point along the sense beam, measuring only the P parameter.
Figure 4:
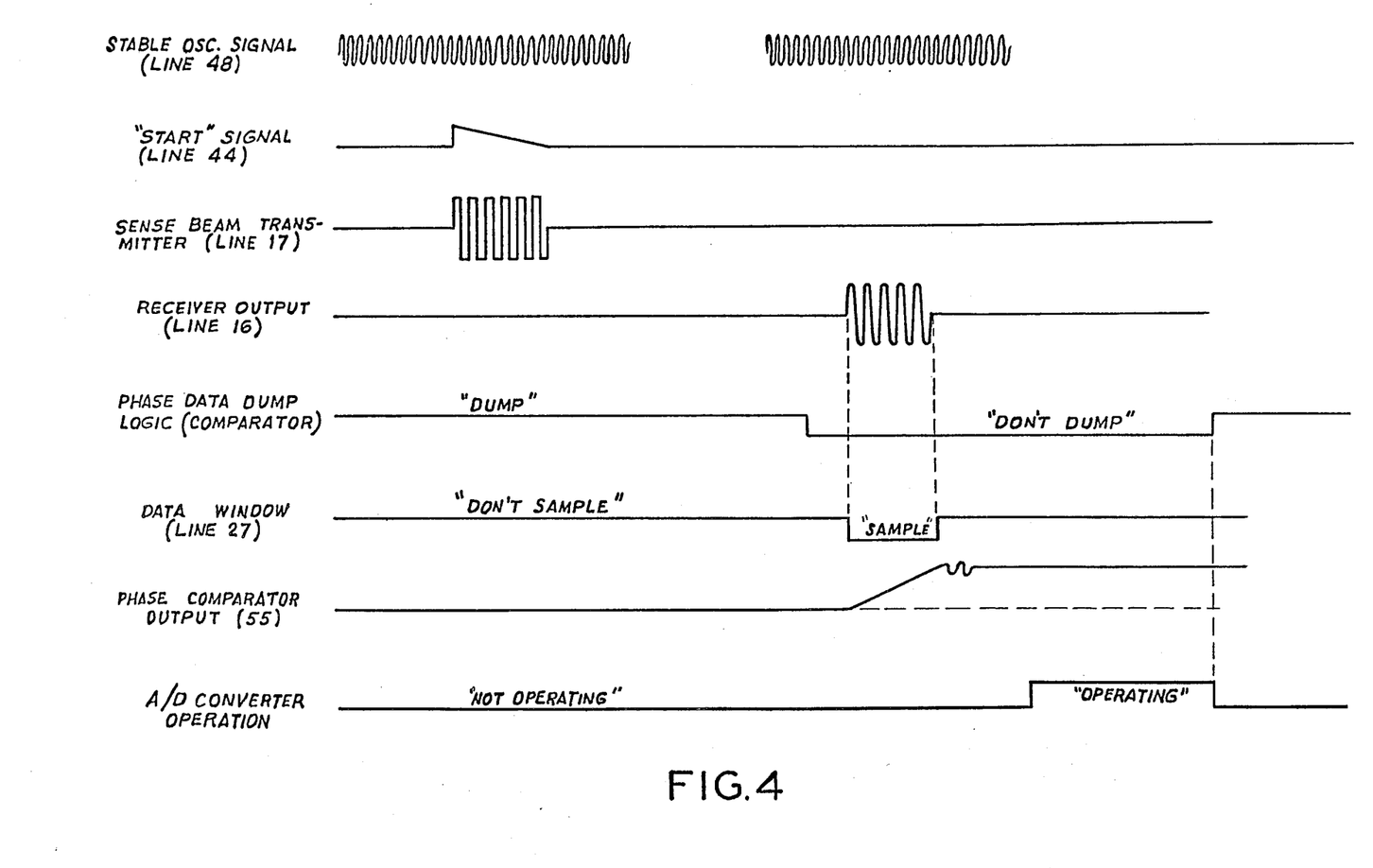
FIG. 4 is a micro-timing for the transmission and reception of a single sense burst.

The second (exciting field) transducer 14 is connected to a high power oscillator 19 by line 37. The master timing control 23 receives a general trigger signal from the body function and line synch signal generator 30 and orders one, or a multiplicity, of bursts from the coherent burst generator 22, via line 44. These bursts are propagated through the tissue, received, sense compared and interpreted as digital numbers and fed (over line 50) into the arithmetic and memory unit 40 which the master timing has also informed via line 43 that these signals are due. These digital numbers are identified as "group A" by the master timing control 23 which has also informed the arithmetic and memory unit 40 of this fact via line 53. All of these numbers are added together and stored as the number "$V_A$". In FIG. 2 an average value for these various measurements is shown as $V_A$ on the fourth line down. The master timing control 23 then activates the power oscillator 19, over line 49, which then heats the sense point 13 by means of transducer 14 which is fed by line 37. The control line 42 indicates to the power oscillator 19 what power level it should produce on the basis of the system's "knowledge" of the media the exciting field 15 is passing through, and thus the amount of power required to excite the sense point 13 the appropriate amount. Thereafter the master timing control 23 again activates the coherent burst generator 22 via line 44 for the same number of times it did before, but in the meantime the master timing control 23 has identified this group, by means of line 53, as "group B". These analog to digital converter numbers are again added to the sum stored as a number "$V_B$", see FIG. 2. This number $V_B$ is the sum of the phase values measured by the system for each successive burst of sense beam in the "B" measurement group. Each of these phase values constitues a measurement of the medium after the heating of the sense point. The difference between $V_A$ and $V_B$ is taken, and so long as the number of bursts measured in each case is the same, the result is the difference between the average phase before and after the excitation, multiplied by the number of measurements. In order to measure the P value, it is only necessary to multiply this difference $V_A - V_B$ by appropriate scaling factors. This number is then transferred by line 54 into the storage and display system 41, and associated with the particular point in space where sense point 13 was located during this set of measurements as indicated by the mechanical positions of the transducers as indicated by line 38.

To make a measurement of the D factor (the rate of cooling of tissue) at this same point in space, for example, the master timing control 23 might order another set of sense bursts through line 44, as shown in FIG. 2, after a predetermined delay $T_C$ has occurred. This delay should be sufficient to permit the temperature profile at sense point 13 to change. These next measurements are again digitized and added together and stored as number "$V_C$". Next, some convenient function of $V_B - V_A$ and $V_C - V_A$ and the delay time $T_C$ is calculated as a measurement of the parameter D. Other measurements of the parameter D may be made by producing later sets of bursts of sense beam measurements and identifying them as the numbers $V_E$, $V_F$, $V_G$, etc., and then comparing them as, for example, the same function of $V_B - V_A$ and $V_E - V_A$ and the delay between B and E, etc. Note that $V_A$ constitutes the base line which must be subtracted from all measurements. $V_B - V_A$ constitutes the magnitude of the initial perturbation, and $V_X - V_A$ constitutes the magnitudes of the remaining perturbations where X is another later set of measurements occurring at time $T_x$ after B. There is some function of $(V_X - V_A)/(V_B - V_A)$ which is proportional to the average rate of decay of the thermal perturbation of the sensing sound beam and is thus a measure of the fluid flow in the tissue.

For example, the biological information gained from the rate of decay of the thermal field, as determined by decay curves such as that shown in FIG. 2, is the perfusion of the tissue, i.e., the number of liters per second of blood flow per kilogram of tissue which is available to carry away the heat.

IV. Modifications and Applications of the Invention

Modifications may be made in the present invention within the scope of the subjoined claims. Some of the modifications are as follows:

1. The reference burst of the sensing beam, instead of occuring before the heating occurs due to the focused exciting beam, may occur after such heating takes place. A multiplicity of bursts, after such heating, may be compared with each other to determine the rate of cooling.

2. The scanning may occur along the sensing beam, which would be stationary. The focal point of the exciting beam would be moved along the fixed sensing beam to provide a scan of the material along the length of the sensing beam. The position of the scanning beam may then be changed and fixed to provide, by a gain moving the focus of the exciting beam along the scanning beam, a second scan along a different line. In this scan technique the heating focused ultrasonic waves may be produced in bursts to correspond to distinct movement of the exciting focal point along the scanning beam. Also, the power in the exciting field may be computer controlled to produce the same intensity at the focus in spite of varying amounts of tissue in between.

3. It is important that the bursts of ultrasonic waves of the sensing beam be identical, i.e., of the same duration, amplitude and frequency. For this purpose the amplitude should be held constant to within one part in 2500. In addition, a comparison may be made as between input (line 17) and output (line 16) amplitudes of each burst, and the correction applied to the output signal of the phase comparator 29, as well as between output signals.

4. Although the above-described embodiment relates to tissue, living or dead, the invention may be used as an inspection device. For example, soft material contained in a hard shell may be inspected without destroying the shell, or one may examine the interior structure of a tree.

5. The present invention may be used with other techniques, for example, holography or echography. The areas of particular interest may be set up and the TAST system of the present invention used to examine in detail such areas. Alternatively, a random or patterned series of spots may be analyzed by TAST to select areas for further investigation.

6. Since the frequency dependence of the P factor of different tumor types, or other material types, differ from one another, one may distinguish specific structures from one another by switching the frequency of the exciting field to one or more different frequencies and making use of this difference in P factor frequency dependence to identify the objects in question.

Identification of the tissue type by P factor and P factor dependence on frequency requires that the intensity of the exciting field at the focus be known. This information must be generated separately for each frequency, so a scan or partial scan for each frequency of exciting field is necessary.

7. The techniques of pattern recognition are developing rapidly in the computer field. One problem in medicine is obtaining data and then making a clinical evaluation, which is a type of pattern recognition, where the patterns are those of specific maladies or specific organs. The computer can do such things more efficiently than the human mind for many types of situations if the proper digital data can be supplied to it.

The present invention provides a number grid in space. It is possible to derive the location of the organ with minimum information and then to state the probability that the position recognition is correct. After its location is established it is then possible to analyze the structure of the organ, and recognize the defects, again stating the probability that the recognition of the defects is correct.

8. One may scan as rapidly as possible with the use of the P factor measurements, and once the tissue geometry becomes clear, make measurements of the blood supply (perfusion) at designed points in the tissue to see how vascular the tumor is at various points. This is another characteristic which distinguishes one tumor from another, so that use of both parameters to evaluate one suspected volume of tissue gives much more useful information than either measurement alone.

9. The blood flow in a large vessel may be measured by marking (heating) a bolus of blood with the exciting field and observing a known distance downstream on that blood vessel with the sensing beam. The perturbation initially seen by the sensing beam would be zero as that beam does not pass through the heated portion of the tissue. As the marked bolus moves downstream, however, it passes through the sensing beam's path and the time of transit of the bolus between the exciting beam focus and the sense beam crossing the blood vessel is indicated by the phase changes detected by the sense beam. This is a direct measure of the velocity of the blood in that vessel.

I claim:

1. A system for ultrasonic inspection of non-moving substance such as a log, said system including
   means to produce a collimated ultrasonic sensing beam directed through said substance, said sensing beam means including an ultrasonic transmitting transducer to produce said collimated beam, an oscillator which is a reference source of continuous waves of ultrasonic frequency, and gating means connected between said source and said beam transmitting transducer to produce coherent bursts of oscillations which are discrete trains of oscillations at ultrasonic frequency to be fed to said beam transmitting transducer from said oscillator,
   an ultrasonic receiving transducer positioned to receive said sensing beam,
   a phase comparison means connected to said receiving transducer and to said reference oscillator to respond to phase changes in the sensing beam caused by transmission through said substance,
   a second ultrasonic transmitting transducer and a second oscillator connected to said second ultrasonic transmitting transducer, said second transmitting transducer positioned to heat said substance along the path of said sensing beam through said substance; and
   timing means to control said sensing beam means and said second transmitting transducer so that they are activated in sequence and not simultaneously to compare the phase changes in the sensing beam through said substance before and after said ultrasonic heating.

2. An instrument as in claim 1 and also including a changeable phase shifter connected to said reference oscillator.

3. An instrument as in claim 1 and also including a propagation path compensation logic means connected to said reference oscillator and to said phase comparison means for the measurement of the transit time of said sense beam with reference to complete oscillations of said reference oscillator to within one sense beam oscillation period.

4. An instrument as in claim 3 wherein said propagation path compensation logic means includes a delay circuit, said delay being based on the reference oscillator frequency which is the same as that transmitted and received as an ultrasonic burst.

5. An instrument as in claim 3 and also including an analog to digital converter connected to said phase comparison means wherein a digital number is generated by said digital converter and by said path length compensation logic means utilizing phase information from said analog to digital converter to which it is connected to obtain a precise value for the sensing beam transit time from said transmitting transducer to said receiving transducer.

6. An instrument as in claim 1 wherein said gating means includes means so that said gating means is phase coherent with the oscillation from said reference oscillator.

7. The instrument of claim 1 wherein the frequency of said reference oscillator is stable to within one part of $1 \times 10^8$ over the sensing beam's transit time.

8. The instrument of claim 1 wherein such phase comparison means contains a data window circuit in timed relationship with said gating circuit means whereby said data window is opened during the arrival of the sense bursts produced by said gating circuit means.

* * * * *